United States Patent
Cohen et al.

(10) Patent No.: US 11,992,533 B2
(45) Date of Patent: May 28, 2024

(54) METHODS OF TREATMENT OF HLA-B27 RELATED INFLAMMATORY DISEASES AND COMPOSITIONS RELATED TO SAME

(71) Applicant: ALMA BIO THERAPEUTICS, Lyons (FR)

(72) Inventors: Irun Cohen, Rehovot (IL); Denis Ravel, Paris (FR); Raanan Margalit, Rehovot (IL); Binah Baum, Lyons (FR)

(73) Assignee: Michael Stalhamer, Edison, NJ (US)

( * ) Notice: Subject to any disclaimer, the term of this patent is extended or adjusted under 35 U.S.C. 154(b) by 0 days.

(21) Appl. No.: 17/673,543

(22) Filed: Feb. 16, 2022

(65) Prior Publication Data
US 2022/0241431 A1    Aug. 4, 2022

Related U.S. Application Data

(63) Continuation of application No. 16/493,242, filed as application No. PCT/IB2018/000408 on Mar. 28, 2018, now abandoned.

(60) Provisional application No. 62/480,171, filed on Mar. 31, 2017.

(51) Int. Cl.
| A61P 19/10 | (2006.01) |
| A61K 48/00 | (2006.01) |
| A61P 1/04  | (2006.01) |
| A61P 19/02 | (2006.01) |
| A61P 29/00 | (2006.01) |

(52) U.S. Cl.
CPC .............. *A61K 48/005* (2013.01); *A61P 1/04* (2018.01); *A61P 19/02* (2018.01); *A61P 29/00* (2018.01)

(58) Field of Classification Search
CPC ........ A61K 48/005; A61P 19/02; A61P 29/00; A61P 1/04
See application file for complete search history.

(56) References Cited

U.S. PATENT DOCUMENTS

| 9,283,265 B2 | 3/2016 | Cohen et al. | |
| 2003/0022438 A1 | 12/2003 | Guild et al. | |
| 2013/0122083 A1* | 5/2013 | Cohen ..................... | A61P 29/00 424/450 |
| 2013/0259876 A1* | 10/2013 | Murphy .................... | A61P 1/04 424/173.1 |
| 2014/0286916 A1* | 9/2014 | Albarani ................ | A61K 35/28 424/93.7 |

FOREIGN PATENT DOCUMENTS

| CN | 104169302 | 11/2014 |
| EP | 2301566 | 3/2011 |
| WO | 2003096967 | 11/2003 |
| WO | 2008115719 | 9/2008 |

OTHER PUBLICATIONS

Marker-Hermann et al., T-Cell Studies in the Spondyloarthropathies, 2000, Current Rheumatology Reports, vol. 2, pp. 297-30 (Year: 2000).*
Jajic, The Role of HLA-B27 in the Diagnosis of Low Back Pain, 1979, Acta orthop., vol. 50, pp. 411-413. (Year: 1979).*
"HLA B27 associated uveitis", Th. Neb, University of Clinic Freiburg, (Oct. 30, 2006), 1-3.
Gough and Simmonds, (2007) "The HLA Region and Autoimmune Disease: Associations and Mechanisms of Action", Current Genomics, vol. 8, No. 7, pp. 453-465.
Gracey, et al., (2016) "Sexual Dimorphism in the TH17 Signature of Ankylosing Spondylitis", Arthritis & Rheumatology, vol. 68, No. 3, pp. 679-689.
Han, et al., (2015) "Th17 Cells in autoimmune diseases", Front. Med., 9(1): pp. 10-19.
McCeigh M. and Cairns, (2006) "Diagnosis and management of ankylosing spondylitis", BMJ, vol. 333, pp. 581-585.
Raychaudhuri, P. Siba and Raychaudhuri, K. Smith, (2017) "Mechanistic rationales for targeting Interleukin-17A in spondyloarthritis", Arthritis Research & Therapy, 19:51, pp. 1-9.
Sieper, Joachim, et al., (2014) "Assessment of short-term symptomatic efficacy of tocilizumab in ankylosing spondylitis: results of randomised, placebo-controlled trials" Ann Rheum Dis;73:95-100.
Sieper, Joachim, et al., (2015), "Sarilumab for the treatment of ankylosing spondylitis: results of a Phase II, randomised, double-blind, placebo-controlled study (ALIGN)", Ann Rheum Dis; 74:1051-1057.
Whitacre, (2001) "Sex differences in autoimmune disease", Nature Immunology, vol. 2, No. 9, pp. 777-780.
Yang, Geng-Ho, (2017) "The Biological Effects of Interleukin-6 and Their Clinical Applications in Autoimmune Diseases and Cancers", Rheumatica Acta: Open Access, 1(1): 006-016.
Bergfeldt, (1997) "HLA-B27-Associated Cardiac Disease" Annals of Internal Medicine, 127:621-629.
Breban et al., (1998), "Animal models and in vitro models for the study of aetiopathogenesis of spondyloarthropathies", Ann Med Interne (Paris), 149:139-141.
Hammer et al., (1990) "Spontaneous Inflammatory Disease in Transgenic Rats Expressing HLA-827 and Human 32m: An Animal Model of HLA-827-Associated Human Disorders", Cell, 63(1):099-1112.
Marker-Hermann et al. (2000) "T-Cell Studies in the Spondyloarthropathies" Current Rheumatology Reports 2: 297-330.
Quintana-Fj et al., (2004) "Inhibition of Adjuvant-Induced Arthritis byDNA Vaccination With the 70-kd or the 90-kdHuman Heat-Shock ProteinImmune Cross-Regulation With the 60-kd Heat-Shock Protein", Arthritis & Rheumatism, 50(11): 3712-3720.
Quintana-Fj et al., (2004) "Network cross-reactivity: DNA vaccination with HSP70 or HSP90 modulates immunity to HSP60 and inhibits adjuvant arthritis", Immunology, 207-213.

(Continued)

*Primary Examiner* — Ali Soroush
(74) *Attorney, Agent, or Firm* — Bozicevic, Field & Francis LLP; Shweta Chandra (57) ABSTRACT

The present disclosure provides methods and compositions for treatment of an HLA-B27-associated autoimmune inflammatory disorder by administration of nucleic acid encoding HSP90 or an active fragment thereof.

20 Claims, 5 Drawing Sheets
Specification includes a Sequence Listing.

(56) References Cited

OTHER PUBLICATIONS

Sartor et al., (1996) "Animal models of intestinal and joint inflammation", Baillieres Clin Rheumatol, 0:55-76.
Taurog et al., (1994) "The Germfree State Prevents Development of Gut and Joint Inflammatory Disease in HLA-B27 Transgenic Rats", J. Exp Med, 180:2359-64.
Wang et al. (2020) "HLA-DR15 Molecules Jointly Shape an Autoreactive T Cell Repertoire in Multiple Sclerosis" Cell 183: 1-39.
Asquith et al., (2016) "Perturbed Mucosal Immunity and Dysbiosis Accompany Clinical Disease in a Rat Model of Spondyloarthritis", Arthritis Rheumatol, 68(9):2151-2162.
Van Tok et al., (2017) "Innate Immune Activation Can Trigger Experimental Spondyloarthritis in HLA-B27/Huβ2m Transgenic Rats", Frontiers in Immunology, 8:1-12.
Song et al., (2011) "Treatment of active ankylosing spondylitis withabatacept: an open-label, 24-week pilot study", Ann Rheum Dis., 70(6):1108-1110.
Quintana et al., (2011) "The HSP60 immune system network", Trends Immunology, 32(2):88-95.
Wendling et al., (2012) "Rituximab Treatment for Spondyloarthritis. A Nationwide Series: Data from the AIR Registry of the French Society of Rheumatology", The Journal of Rheumatology, 39(12):2327-2331.
Ringrose J H., (1999) "HLA-B27 associated spondyloarthropathy, an autoimmune disease based on crossreactivity between bacteria and HLA-B27?", Ann Rheum Dis., 58:598-610.
Quintana et al., (2004) "Inhibition of Adjuvant-Induced Arthritis by DNA Vaccination With the 70-kd or the 90-kd Human Heat-Shock Protein", Arthritis & Rheumatism, 50(11):3712-3720.
Sieper et al., (2014) "Assessment of short-term symptomatic efficacy of tocilizumab in ankylosing spondylitis: results of randomised, placebo-controlled trials", Ann Rheum Dis., 73:95-100.
Sieper et al., (2015) "Sarilumab for the treatment of ankylosing spondylitis: results of a Phase II, randomised, double-blind, placebo-controlled study (ALIGN)", Ann Rheum Dis., 74:1051-1057.
Whitacre, Caroline (2001) "Sex differences in autoimmune disease", Nature Immunology, 2(9):777-780.
Sibley, Cailin (2016) "Autoinflammation and HLA-B27: More than an Antigen", Ocul Immunol Inflamm., 24(4):460-469.
May et. al., (2003) "CD8αβ T cells are not essential to the pathogenesis of arthritis or colitis in HLA-B27 transgenic rats", Journal of Immunology, 170(2):1099-1105.
Taurog et. al., (2009) "Spondylarthrites in HLA-B27/human beta2-microglobulin-transgenic rats is not prevented by lack of CD8", Arthritis Rheum., 60(7):1977-1984.

\* cited by examiner

SEQUENCE LISTING

<160> NUMBER OF SEQ ID NOS: 1

<210> SEQ ID NO 1
<211> LENGTH: 732
<212> TYPE: PRT
<213> ORGANISM: Homo sapiens

<400> SEQUENCE: 1

```
Met Pro Glu Glu Thr Gln Thr Gln Asp Gln Pro Met Glu Glu Glu
1               5                   10                  15

Val Glu Thr Phe Ala Phe Gln Ala Glu Ile Ala Gln Leu Met Ser Leu
                20                  25                  30

Ile Ile Asn Thr Phe Tyr Ser Asn Lys Glu Ile Phe Leu Arg Glu Leu
                35                  40                  45

Ile Ser Asn Ser Ser Asp Ala Leu Asp Lys Ile Arg Tyr Glu Ser Leu
            50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
                100                 105                 110

Ser Gly Thr Lys Ala Phe Met Glu Ala Leu Gln Ala Gly Ala Asp Ile
            115                 120                 125

Ser Met Ile Gly Gln Phe Gly Val Gly Phe Tyr Ser Ala Tyr Leu Val
    130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
                180                 185                 190

Asp Gln Thr Glu Tyr Leu Glu Glu Arg Arg Ile Lys Glu Ile Val Lys
            195                 200                 205

Lys His Ser Gln Phe Ile Gly Tyr Pro Ile Thr Leu Phe Val Glu Lys
    210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Glu Glu Lys Lys Asp Gly
                260                 265                 270

Asp Lys Lys Lys Lys Lys Lys Ile Lys Glu Lys Tyr Ile Asp Gln Glu
            275                 280                 285

Glu Leu Asn Lys Thr Lys Pro Ile Trp Thr Arg Asn Pro Asp Asp Ile
    290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
                340                 345                 350

Glu Asn Arg Lys Lys Lys Asn Asn Ile Lys Leu Tyr Val Arg Arg Val
            355                 360                 365
```

```
Phe Ile Met Asp Asn Cys Glu Glu Leu Ile Pro Glu Tyr Leu Asn Phe
    370             375             380
Ile Arg Gly Val Val Asp Ser Glu Asp Leu Pro Leu Asn Ile Ser Arg
385             390             395             400
Glu Met Leu Gln Gln Ser Lys Ile Leu Lys Val Ile Arg Lys Asn Leu
                405             410             415
Val Lys Lys Cys Leu Glu Leu Phe Thr Glu Leu Ala Glu Asp Lys Glu
            420             425             430
Asn Tyr Lys Lys Phe Tyr Glu Gln Phe Ser Lys Asn Ile Lys Leu Gly
        435             440             445
Ile His Glu Asp Ser Gln Asn Arg Lys Lys Leu Ser Glu Leu Leu Arg
    450             455             460
Tyr Tyr Thr Ser Ala Ser Gly Asp Glu Met Val Ser Leu Lys Asp Tyr
465             470             475             480
Cys Thr Arg Met Lys Glu Asn Gln Lys His Ile Tyr Tyr Ile Thr Gly
                485             490             495
Glu Thr Lys Asp Gln Val Ala Asn Ser Ala Phe Val Glu Arg Leu Arg
            500             505             510
Lys His Gly Leu Glu Val Ile Tyr Met Ile Glu Pro Ile Asp Glu Tyr
        515             520             525
Cys Val Gln Gln Leu Lys Glu Phe Glu Gly Lys Thr Leu Val Ser Val
    530             535             540
Thr Lys Glu Gly Leu Glu Leu Pro Glu Asp Glu Glu Glu Lys Lys Lys
545             550             555             560
Gln Glu Glu Lys Lys Thr Lys Phe Glu Asn Leu Cys Lys Ile Met Lys
                565             570             575
Asp Ile Leu Glu Lys Lys Val Glu Lys Val Val Val Ser Asn Arg Leu
            580             585             590
Val Thr Ser Pro Cys Cys Ile Val Thr Ser Thr Tyr Gly Trp Thr Ala
        595             600             605
Asn Met Glu Arg Ile Met Lys Ala Gln Ala Leu Arg Asp Asn Ser Thr
    610             615             620
Met Gly Tyr Met Ala Ala Lys Lys His Leu Glu Ile Asn Pro Asp His
625             630             635             640
Ser Ile Ile Glu Thr Leu Arg Gln Lys Ala Glu Ala Asp Lys Asn Asp
                645             650             655
Lys Ser Val Lys Asp Leu Val Ile Leu Leu Tyr Glu Thr Ala Leu Leu
            660             665             670
Ser Ser Gly Phe Ser Leu Glu Asp Pro Gln Thr His Ala Asn Arg Ile
        675             680             685
Tyr Arg Met Ile Lys Leu Gly Leu Gly Ile Asp Glu Asp Asp Pro Thr
    690             695             700
Ala Asp Asp Thr Ser Ala Ala Val Thr Glu Glu Met Pro Pro Leu Glu
705             710             715             720
Gly Asp Asp Asp Thr Ser Arg Met Glu Glu Val Asp
                725             730
```

METHODS OF TREATMENT OF HLA-B27 RELATED INFLAMMATORY DISEASES AND COMPOSITIONS RELATED TO SAME

CROSS-REFERENCE TO RELATED APPLICATIONS

This application is a continuation of U.S. application Ser. No. 16/493,242 filed on Sep. 11, 2019 which application is a 371 of international Application No. PCT/M2018/00040 filed on Mar. 28, 2018 which application claims priority benefit to U.S. Provisional Application No. 62/480,171, filed Mar. 31, 2017, the disclosure of which is incorporated herein by reference in its entirety.

INCORPORATION BY REFERENCE OF SEQUENCE LISTING PROVIDED AS A TEXT FILE

A Sequence Listing is provided herewith in a text file, ALMA-002WO Seq List_ST25, created on Jun. 14, 2018 and having a size of 7000 bytes. The contents of the text file are incorporated herein by reference in its entirety.

INTRODUCTION

The first human leukocyte antigen (HLA) haplotype association with inflammatory disease was discovered in 1972 in which the HLA type HLA-B27 was correlated with ankylosing spondylitis. This remains one of the strongest known associations of disease with HLA-B27. Since then, more than 100 disease associations have been made, including spondyloarthropathies (e.g., ankylosing spondylitis, reactive arthritis (also known as Reiter syndrome), psoriatic arthritis, and enteropathic arthritis), many ocular diseases and systemic diseases with specific ocular manifestations, and as well as inflammatory diseases of the gastrointestinal tract (e.g., inflammatory bowel disease).

There is a need for effective therapies for relief of one or more symptoms of autoimmune inflammatory disorders in HLA-B27 positive subjects.

SUMMARY

The present disclosure provides methods and compositions for treatment of an HLA-B27-associated autoimmune inflammatory disorder by administration of nucleic acid encoding HSP90 or an active fragment thereof.

Accordingly, the present disclosure provides methods for treating or preventing an autoimmune inflammatory disease in an HLA-B27 positive subject, the method comprising administering to a subject having or at risk of an autoimmune inflammatory disease and who is positive for HLA-B27 a composition comprising a nucleic acid molecule encoding a mammalian heat shock protein 90 (HSP90), or an active fragment thereof, wherein the nucleic acid molecule is operatively linked to one or more transcription control sequences, wherein the administering treats the inflammatory disease in the subject.

In some embodiments, the autoimmune inflammatory disease is an inflammatory joint disease, e.g., a spondyloarthropathy, such as, for example, anklyosing spondylitis, reactive arthritis, psoriatic arthritis or enteropathic arthritis. In some embodiments the inflammatory joint disease is juvenile spondarthritis, undifferentiated spondarthritis or isolated peripheral enthesitis.

In some embodiments, the autoimmune inflammatory disease is an ocular disorder, such as uveitis or age-related macular degeneration. In some embodiments, the uveitis is acute anterior uveitis or posterior uveitis.

In some embodiments, the autoimmune inflammatory disease is an inflammatory disease of the gastrointestinal tract, e.g., inflammatory bowel disease, ulcerative colitis, or Crohn's disease.

In some embodiments, the autoimmune inflammatory disease is Behcet disease.

In some embodiments the autoimmune inflammatory disease is a cardiovascular disease.

In any of the above embodiments, the subject can be a subject that is at risk of the autoimmune inflammatory disorder.

In any of the above embodiments, the subject can be a subject has been diagnosed as having the autoimmune inflammatory disorder.

In any of the above embodiments, the mammalian HSP90 can be human HSP90.

In any of the above embodiments, the subject can be a human.

In any of the above embodiments, administration can be by injection, e.g., intramuscular injection.

In any of the above embodiments, the composition can be administered in an amount of from about 0.005 mg/kg to about 1 mg/kg of the nucleic acid molecule encoding the mammalian HSP90, or an active fragment thereof, to the body weight of the subject. In related embodiments, the composition is administered in an amount of from about 0.01 mg/kg to about 0.5 mg/kg of the nucleic acid molecule encoding the mammalian HSP90, or an active fragment thereof, to the body weight of the subject. In further related embodiments, the composition is administered in an amount of from about 0.10 mg/kg to about 0.30 mg/kg of the nucleic acid molecule encoding the mammalian HSP90, or an active fragment thereof, to the body weight of the subject.

In any of the above embodiments, the composition can be administered weekly.

In any of the above embodiments, the composition can be administered for a period of at least 4 weeks.

In some embodiments, the nucleic acid molecule is not encapsulated.

In some embodiments, the nucleic acid molecule is not contained in a virus.

In any of the above embodiments, the composition can comprise a pharmaceutically acceptable alkali metal salt, such as sodium chloride.

In some embodiments, the composition comprises a delivery vehicle selected from the group consisting of a liposome, a micelle, and an emulsion.

In some embodiments, the composition comprises a lipid particle.

In some embodiments, the composition comprises a catioinic lipid, polyethylene glycol, polylysine, poloxamer, chitosan, polyL glutamate, or poly(lactide-co-glycolide) (PLG).

The present disclosure also provides compositions comprising an HSP90-encoding nucleic acid for use in treatment of an autoimmune inflammatory disorder in an HLA-B27 positive subject.

The present disclosure also provides for use of an HSP90-encoding nucleic acid in the manufacture of a medicament for in treatment of an autoimmune inflammatory disorder in an HLA-B27 positive subject.

Before the present invention is described further, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a nucleic acid molecule" includes a plurality of nucleic acid molecules and reference to "an injection" includes reference to one or more injections and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Definitions

"HLA-B27" refers to the human leukocyte antigen (HLA) B27 (including subtypes B*2701-2759), is a class I surface antigen encoded by the B locus in the major histocompatibility complex (MHC) on chromosome 6.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "control element" or "control sequence" refers to a nucleotide sequence involved in an interaction of molecules that contributes to the functional regulation of a polynucleotide, including replication, transcription, translation, or degradation of the polynucleotide in a host cell (e.g., in a eukaryotic host cell, e.g., a human host cell). The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to covalent connection of genetic elements, wherein the genetic elements are provided in a relationship permitting them to operate in a desired manner. For instance, a promoter is operatively linked to a coding region if the promoter facilitates initiation of transcription of the coding sequence. There may be intervening residues between the promoter and coding region so long as this functional relationship is maintained.

An "expression vector" refers to a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

The terms "patient" or "subject" are used interchangeably to refer to a human or a non-human animal (e.g., a mammal). In the context of an HLA-B27 positive subject, such subjects are generally human subjects or non-human animals genetically modified to express HLA-B27.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering IL-10 or a pharmaceutical composition comprising IL-10) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

A "therapeutically effective amount" or "efficacious amount" refers to the amount of an agent (e.g., an HSP90-encoding nucleic acid) that, when administered to a mammal or other subject for treating a disease, is sufficient to effect such treatment for the disease. The "therapeutically effective amount" will vary depending on the agent (e.g., the HSP90-encoding nucleic acid and/or the expression construct used to delivery the HSP90-encoding nucleic acid), as well as patient factors such as the disease and its severity and the age, weight, etc., of the subject to be treated.

The phrase "therapeutically effective amount" encompassed administration of an agent (e.g., an HSP90-encoding nucleic acid) to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like.

DETAILED DESCRIPTION OF EXAMPLES OF EMBODIMENTS

The present invention is based on the discovery that DNA-encoding HSP90 is effective as a therapeutic in the treatment of subjects who are HLA-B27 positive and have, or at risk of, an autoimmune inflammatory disease associated with HLA-B27 positive status.

Heat Shock Protein 90 (HSP90)

In general, the methods of the present disclosure involve administration of a nucleic acid encoding a heat shock protein 90 (HSP90) to a subject so that the HSP90-encoding nucleic acid provides for production of HSP90 protein in the host. Such constructs can be a DNA construct in which the HSP90-encoding DNA is operably linked to a promoter that facilitates expression in the subject.

The HSP90 encoded by the nucleic acid of the construct can be any suitable HSP90, or an active fragment thereof, e.g., a mammalian HSP90 or active fragment thereof, e.g., a human HSP90, rat HSP90, or mouse HSP90, or an active fragment thereof. The nucleic acid sequence encoding the mammalian heat shock proteins may include DNA, RNA, or derivatives of either DNA or RNA with the proviso such are amenable to production of the encoded HSP90 protein gene product in a host cell, e.g., a human cell. The nucleic acid sequence encoding the HSP90 can be obtained from a natural source, either as encoding a full-length HSP90 or a portion thereof. A nucleic acid molecule can also be produced using recombinant DNA technology (e.g., polymerase chain reaction (PCR) amplification, cloning) or chemical synthesis. Nucleic acids encoding HSP90 include naturally-occurring HSP90-encoding nucleic acids and homologues thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to provide for production a functional HSP90 or an active fragment thereof in a cell of the subject to whom it is administered.

Where the subject is human, a nucleic acid encoding a human HSP90 (either full-length or an active fragment thereof) is of particular interest. The human HSP90 can be either the alpha isoform or the beta isoform. The amino acid sequences of examples of human HSP0 proteins suitable for use in the present methods include, for example, NCBI reference sequence NP_001017963 (heat shock protein HSP 90-alpha isoform 1) and NCBI reference sequence NP_005339.3 (heat shock protein HSP 90-alpha isoform 2). The amino acid sequence of an example of a full-length human HSP90 protein is provided below:

```
                                            (SEQ ID NO: 1)
MPEETQTQDQPMEEEEVETFAFQAEIAQLMSLIINT

FYSNKEIFLRELISNSSDALDKIRYESLTDPSKLD

SGKELHINLIPNKQDRTLTIVDTGIGMTKADLINN
```

```
LGTIAKSGTKAFMEALQAGADISMIGQFGVGFYSA

YLVAEKVTVITKHNDDEQYAWESSAGGSFTVRTDT

GEPMGRGTKVILHLKEDQTEYLEERRIKEIVKKHS

QFIGYPITLFVEKERDKEVSDDEAEEKEDKEEEKE

KEEKESEDKPEIEDVGSDEEEEKKDGDKKKKKKIK

EKYIDQEELNKTKPIWTRNPDDITNEEYGEFYKSL

TNDWEDHLAVKHFSVEGQLEFRALLFVPRRAPFDL

FENRKKKNNIKLYVRRVFIMDNCEELIPEYLNFIR

GVVDSEDLPLNISREMLQQSKILKVIRKNLVKKCL

ELFTELAEDKENYKKFYEQFSKNIKLGIHEDSQNR

KKLSELLRYYTSASGDEMVSLKDYCTRMKENQKHI

YYITGETKDQVANSAFVERLRKHGLEVIYMIEPID

EYCVQQLKEFEGKTLVSVTKEGLELPEDEEEKKKQ

EEKKTKFENLCKIMKDILEKKVEKVVVSNRLVTSP

CCIVTSTYGWTANMERIMKAQALRDNSTMGYMAAK

KHLEINPDHSIIETLRQKAEADKNDKSVKDLVILL

YETALLSSGFSLEDPQTHANRIYRMIKLGLGIDED

DPTADDTSAAVTEE1VIPPLEGDDDTSRMEEVD.
```

Any suitable constructs to facilitate delivery of the HSP-encoding nucleic acid into a host cell, particularly a human host cell, to facilitate expression in the host cell can be used. Suitable constructs include plasmids.

In some embodiments, the HSP90-encoding construct does not contain a CpG motif, which may be defined by the generic formula 5'-$X_1$CG$X_2$-3', wherein X1 and X2 represent any nucleotide, and the central CG dinucleotide is unmethylated. Examples of CpG motif-containing sequences include nucleic acid having a sequence of the formulae 5'-RRCGYY-3', 5'-RTCGYY-3', 5'-RRCGYYCG-3', 5'-RTCGYYCG-3', wherein the "CG" are unmethylated CpG dinucleotides, R represents a purine (A or G) and Y represents a pyrimidine (C or T).

The HSP90-encoding constructs generally include a nucleic acid sequence encoding an HSP90 (or active fragment thereof), e.g., a human HSP90, operatively linked to one or more transcription control elements in an expression construct. Transcription control elements include nucleic acids having sequences that facilitate control of initiation, elongation, and termination of transcription. Transcription control elements include promoters, enhancers, operators and repressors. Of particular interest are transcription control elements that facilitate expression in a mammalian cell, particularly a human cell. Promoters of interest in the present constructs include constitutive promoters, inducible, promoters, and tissue-specific promoters, with constitutive promoters being of particular interest. Examples of promoters that can find use in the constructs of the present disclosure to provide for expression of HSP90 in a subject include, but at not necessarily limed to, viral promoters, such as CMV promoters, RSV promoters, retroviral promoters, and SV-40 promoters.

Examples of eukaryotic expression constructs for use in the methods of the present disclosure include: pcDNA3, pcDNA3.1(+/−), pZeoSV2(+/−), pSecTag2, pDisplay, pEF/myc/cyto, pCMV/myc/cyto, pCR3.1, pCI, pBK-RSV, pBK-CMV, pTRES or their derivatives.

Formulations

The HSP90-encoding constructs can be provided in any formulation suitable for administration to a subject, e.g., suitable for administration of a human subject.

Compositions suitable for administration to a subject can include the HSP90-encoding construct and a pharmaceutically acceptable carrier. As used herein, "pharmaceutically acceptable carrier" includes any material which, when combined with an HSP-encoding construct of the present disclosure, retains the biological activity and improves stability of the construct without causing significant adverse reactions. Examples include, but are not limited to, any of the standard carriers such as an isotonic solution of a pharmaceutically acceptable alkali metal salt (e.g., sodium chloride), a phosphate buffered saline (PBS) solution, water, Ringer's solution, dextrose solution, emulsions such as oil/water emulsion, and various types of wetting agents. Aqueous carriers can contain suitable auxiliary substances required to approximate the physiological conditions of the recipient, for example, by enhancing chemical stability and isotonicity. Examples of additives of interest in formulation of the present disclosure include, but are not limited to, sodium citrate, malic acid, ethanol, and PLURONIC F-68®. Additional examples of additives include, for example, pharmaceutically acceptable salts (e.g., sodium acetate, sodium lactate, potassium chloride, calcium chloride), and preservatives. In general formulations are sterile.

Compositions of interest a include a sterile formulation comprising HSP90-encoding nucleic acid (e.g., HSP90-encoding DNA, e.g., in an expression construct operably linked to a promoter, such as a strong constitutive promoter (e.g., CMV)) formulated with 0.9% pharmaceutically acceptable alkali metal salt (e.g., sodium salt, e.g., NaCl).

HSP90-encoding nucleic acid can optionally formulated with a lipid carrier, e.g., so as to be provided as a payload in a stabilized lipid particle, as in a complex with a cationic lipid, e.g., in a liposome or micelle. In such embodiments, the lipid carrier can be modified (e.g., by manipulating the chemical formula of the lipid portion of the delivery vehicle and/or providing a compound capable of targeting the lipid to a target site, for example, a target cell type so as to provide for interaction of lipid carrier (or, for example, other liposome component) with a molecule on the surface of the cell. Suitable targeting compounds include ligands capable of selectively binding another molecule at a particular site. Examples of such ligands include antibodies, antigens, receptors and receptor ligands.

HSP90-encoding nucleic acids can optionally be formulated with a suitable polymer, such as polyethylene glycol, polylysine, poloxamer, Chitosan, polyL glutamate, poly (lactide-co-glycolide) (PLG).

The components of the formulations of the HSP90-encoding nucleic acid can be selected according to a variety of factors, such as the route of administration. For example, where the formulation is to be administered transdermally or topically, the formulation can include absorption enhancers (e.g., DMSO) or other components to promote transport of the nucleic acid across the skin.

In some embodiments, the HSP90-encoding nucleic acid is not encapsulated (e.g., within a liposome). In some the HSP90-encoding nucleic acid is not contained in a viral particle. In some embodiments, the nucleic acid is "naked", i.e., is not encapsulated (e.g., within a liposome) and is not contained in a viral particle.

The HSP90-encoding nucleic acid construct may be provided in a sterile container (e.g., a syringe) and, optionally, may be lyophilized and reconstituted (e.g., with sterile PBS) prior to administration.

Subjects for Treatment

The methods of the present disclosure generally involve treatment of HLA-B27 positive human subjects who have, or who are at risk of, an autoimmune inflammatory disease. "HLA-B27-associated disease" refers to the observation that bearing the HLA-B27 allele carries a statistically significant increased risk of developing the disease compared to persons who do not bear the HLA-B27 allele. HLA-B27 positive subjects include those who express any subtype of HLA-B27, e.g., any of HLA-B27 subtypes B*2701-2759, with the subtype HLA-B*2705 being of particular interest.

HLA-B*27:05 (specifically the HLA-B*27:0502 allele) is the most widely distributed disease-associated subtype in the world. Other common disease-associated subtypes include HLA-B*27:02 (Mediterranean populations) and HLA-B*27:04 (Chinese and other Asian populations). HLA-B*27:01, HLA-B*27:03, HLA-B*27:07, HLA-B*27:08, HLA-B*27:10, HLA-B*27:13, HLA-B*27:14, HLA-B*27:15, HLA-B*27:19, HLA-B*27:23, HLA-B*27:24, HLA-B*27:25 and HLA-B*27:49 have also been implicated as associated with disease. It will be understood that ancestry can influence the strength of association of an HLA-B27 subtype and disease incidence. It should be noted that HLA-B*27:05 and HLA-B*27:02 confer about equal susceptibility to ankylosing spondylitis (AS) in Caucasian populations. Among Chinese populations, HLA-B*27:04 has been demonstrated to show a stronger association with AS than HLA-B*27:05.

HLA-B27 status (i.e., HLA-B27 positive or HLA-B27 negative) can be determined by any suitable method accepted in the art for determining HLA status. For example, HLA-B27 status can be determined by detection of the HLA-B27 antigen in a sample (e.g., blood sample) obtained from the subject, e.g., using a suitable commercially available detection reagent and method (e.g., an anti-HLA-B27 antibody, and in an ELISA or flow cytometry assay). An example of a suitable assay is the ELISA sandwich assay available from LSBio (LifeSpan BioSciences, Inc.) (Human HLA-B27 ELISA Kit, Catalog No. LS-F21903) for antibody-based detection of HLA-B27 in a plasma or serum sample of a human subject.

A HLA-B27 positive status has been associated with a number of autoimmune inflammatory diseases, and thus the methods of the present disclosure contemplates treatment of individuals having, or at risk of having, such HLA-B27-associated autoimmune inflammatory diseases. HLA-B27 positive subjects may be either male or female, and may be of any age, including an age at which risk of onset of an HLA-B27-associated autoimmune inflammatory disorder is increased in an HLA-B27 subject as compared to an HLA-B27 negative subject.

Examples of HLA-B27-associated autoimmune inflammatory diseases amenable to treatment according to the methods of the present disclosure include inflammatory joint diseases, such as spondyloarthropathies (e.g., seronegative spondyloarthropathies (where the subject is seronegative for rheumatoid factor). Examples of HLA-B27-associated spondyloarthropathies include anklyosing spondylitis, reactive arthritis, psoriatic arthritis, enteropathic arthritis, undifferentiated spondyloarthropathy, and juvenile idiopathic arthritis (JIA, including late-onset oligoarticular JIA). Other examples of HLA-B27-associated inflammatory joint diseases include juvenile spondarthritis, undifferentiated spondarthritis or isolated peripheral enthesitis. Notably, not all subjects who have such autoimmune inflammatory joint diseases are HLA-B27 positive. In other words not all subjects having, for example, axial spondylitis (e.g., ankylosing spondylitis), reactive arthritis, psoriatic arthritis and enteropathic are HLA-B27 positive, and thus HLA-B27 positive subjects are a subset of subjects having these diseases.

Other examples of HLA-B27-associated autoimmune inflammatory diseases amenable to treatment according to the methods of the present disclosure include ocular disorders, such as uveitis, e.g., anterior uveitis (e.g., acute anterior uveitis (AAU)), posterior uveitis, age-related macular degeneration (ARMD), conjunctivitis, keratitis, vitritis, retinal vasculitis, dry eye, keratitis, episcleritis/scleritis and peripheral ulcerative keratitis). Uveitis may be present in a subject having or at risk of ankylosing spondylitis, reactive arthritis (also known as Reiter's syndrome), undifferentiated spondyloarthropathy, or psoriatic arthropathy.

Other examples of HLA-B27-associated autoimmune inflammatory diseases amenable to treatment according to the methods of the present disclosure include inflammatory disease of the gastrointestinal tract such as inflammatory bowel disease, ulcerative colitis, or Crohn's disease. Notably, not all subjects who have such autoimmune inflammatory gastrointestinal diseases are HLA-B27 positive. In other words not all subjects having inflammatory bowel disease, ulcerative colitis, or Crohn's disease are HLA-B27 positive, and thus HLA-B27 positive subjects are a subset of subjects having these diseases.

Other examples of HLA-B27-associated autoimmune inflammatory diseases amenable to treatment according to the methods of the present disclosure include HLA-B27-associated autoimmune inflammatory skin disease, such as psoriasis associated with psoriatic arthritis, which may be characterized by psoriasiform skin lesions and/or nail lesions.

Other examples of HLA-B27-associated autoimmune inflammatory diseases amenable to treatment according to the methods of the present disclosure include Behcet disease.

Other examples of HLA-B27-associated autoimmune inflammatory diseases amenable to treatment according to the methods of the present disclosure include cardiovascular disease, e.g., a cardiac syndrome that involves severe conduction system abnormalities plus aortic regurgitation. See, e.g., Bergfeldt (1997) Ann Intern Med. 127:621-629.

Other examples of HLA-B27-associated autoimmune inflammatory diseases amenable to treatment according to the present methods include fibrosis, e.g., pulmonary fibrosis, e.g., upper lobe pulmonary fibrosis.

Subjects amenable to therapy according to the methods of the present disclosure include those who present with one or more HLA-B27-associated autoimmune inflammatory diseases, e.g., such that the subject presents symptoms of both an autoimmune inflammatory joint disease and an autoimmune inflammatory gastrointestinal disease. For examples, subjects having have an enteropathic arthropathy or spondylitis have an autoimmune inflammatory joint disease that is associated with, e.g., Crohn's disease or ulcerative colitis. In another example, subjects may have an autoimmune inflammatory ocular disease, such as uveitis, which is associated with an autoimmune inflammatory joint disease. Examples of HLA-B27 autoimmune inflammatory diseases that can be associated, e.g., occur in the same subject where a second disease may occur on or after onset of a first disease, are provided in the table below.

TABLE

Examples of Associations of HLA-B27-Associated Autoimmune Inflammatory Diseases

| Condition | Ocular Involvement |
|---|---|
| Ankylosing Spondylitis | Acute anterior uveitis (AAU) |
| | Conjunctivitis |
| Reiter's Syndrome and Reactive Arthritis | Conjunctivitis |
| | Anterior uveitis Keratitis |
| Undifferentiated Spondyloarthropathy | Anterior uveitis (acute or chronic) |
| | Vitritis |
| | Retinal Vasculitis |
| Psoriatic Arthropathy | Anterior uveitis Conjunctivitis Dry eye Keratitis |
| Inflammatory Bowel Disease | Conjunctivitis |
| | Episcleritis/Scleritis |
| | Anterior Uveitis |
| | Vitritis |
| | Retinal vasculitis |
| | Peripheral ulcerative keratitis |

Treatment Regimen

The HSP90-encoding constructs of the present disclosure are generally administered to an HLA-B27 positive subject having, or at risk of, an autoimmune inflammatory disorder in an amount and for a period of time to provide for improvement in at least one disease symptom. As will be appreciated, the dosage regiment will vary according to a number of factors including, but not limited to, the HLA-B27-associated disease to be treated, severity of the disease, the age and health of the patient, and the like.

The HSP90-encoding constructs may be administered according to any suitable conventional and pharmaceutically acceptable route of administration. Such routes include any suitable parenteral route, including by injection or transdermal delivery, e.g., intramuscular injection, subcutaneous injection, intradermal injection, topical administration, and intravenous administration. Enteral routes of administration are also contemplated (e.g., intranasal and other routes of effective inhalation routes). Administration by injection, particularly by intramuscular injection is of particular interest.

The HSP90-encoding construct can be administered in a single dose, or in multiple doses, and may encompass administration of additional doses, to elicit and/or maintain the desired effect. The amount administered (e.g., by injection, e.g., by intramuscular or subcutaneous injection) can be from about 0.001 mg/kg body weight to about 1 mg/kg body weight, from about 0.005 mg/kg body weight to about 0.5 mg/kg body weight, from about 0.01 mg/kg body weight to about 0.4 mg/kg body weight, from about from about 0.20 mg/kg body weight to about 0. 30 mg/kg body weight, of HSP90-encoding nucleic acid. Doses of HSP90-encoding nucleic acid can be from about 0.1 mg to about 30 mg, from about 0.2 mg to about 25 mg, from about 0.3 mg to about 20 mg, or from about 0.5 mg to about 15 mg per subject (e.g., where subject is from about 65 kg to about 70 kg). In some embodiments the dose of HSP90-encoding nucleic acid administered is about 0.20 mg/kg to about 0.30 mg/kg, or 0.25 mg/kg of HSP90-encoding nucleic acid per body weight of the subject. In some embodiments, the dose of HSP90-encoding nucleic acid is from about 0.2 mg to about 20 mg, or from about 0.5 mg to about 15 mg per subject. For example, the dose can be from about 0.001 to 1 mg/kg corresponding to 0.06 to 65 mg per subject for a body weight of 65 kg subject.

The HSP90-encoding nucleic acid can be administered daily, every other day, twice per week, once per week, every other week, or once per month, with weekly doses being of particular interest. The HSP90-encoding nucleic acid can be administered for a period of at least 3 days, at least 5 days, at least 1 week, at least 2 weeks, at least 3 weeks, at least 4 weeks, at least 5 weeks, or at least 6 weeks or more.

EXAMPLES

The following examples are provided in order to demonstrate and further illustrate certain embodiments and aspects of the present invention and are not to be construed as limiting the scope thereof.

Methods and Materials

Animals

Human leukocyte antigen B27 (HLA-B27) transgenic rats, which are transgenic for HLA-B*2705 and human 32-microglobulin, have previously been described, for example by Taurog et al. (J. Exp Med 1994 180:2359-64) and Hammer et al. (Cell 1990 63:1099-1112). Transgenic rats, overexpressing the human HLA-B27 and β2-microglobulin proteins, develop lesions of the gastrointestinal system, the joints, the skin, and the gonads, which seem similar to the spondyloarthropathies in humans that have been associated with the HLA-B27 and β2-microglobulin genes. The gastrointestinal inflammation is mostly limited to the mucosa and submucosa, exhibiting histological features similar to those present in inflammatory bowel disease (IBD) (Taurog et al. J. Exp Med 1994 180:2359-64; Hammer et al. Cell 1990 63:1099-1112; Sartor et al. Baillieres Clin Rheumatol 1996 10:55-76; Breban et al. Ann Med Interne (Paris) 1998 149:139-141). Chronic intestinal inflammation is the first to occur, with clinical signs of diarrhea apparent after 12 weeks of age.

The HLA-B27 transgenic rats uniformly develop a progressive inflammatory disease similar to the HLA B27-associated human spondyloarthropathies (e.g,. anklyosing spondylitis, reactive arthritis, and arthritis associated with inflammatory bowel disease), including colitis, enteritis, arthritis, male genital inflammation, and psoriasiform skin and nail lesions. HLA-B27 transgenic rats developed inflammatory disease involving the gastrointestinal tract, peripheral and vertebral joints, male genital tract, skin, nails, and heart. Accordingly, the HLA-B27 transgenic rat is an art-accepted model of human HLA-B27-associated inflammatory diseases.

Male and female HLA-B27 rats were raised under pathogen-free conditions in the accredited facilities at Institut Pasteur in Lille and those of the Nord-Pas de Calais Ethical Committee for animal use. The animals were maintained at an ambient temperature of 20±5° C. with relative humidity of 50±20%. The animal housing were maintained at a light and dark cycle of 12 hours each and the ventilation was set to approximately 12 cycles/hour using filtered, non-recycled air.

Five animals were housed per cage with free access to standard mice chow and tap water. The experiments were performed using animals that were eight-week old at the beginning of the experiments. Representative eight week old animals weighted 100 g and representative twelve week old animals weighed 280 g. The experiments were performed and the animals were maintained according to governmental guidelines (articles R214-87-R214-137 code rural update 13 Feb. 2013 according to European directive 2010/63/UE).

The animals were randomized in two groups. At the beginning of the study, each animal received a unique identity number. The animals were individually identified by an ear tattoo at the breeder's facility. Eight animals were randomly assigned to group 1 and another eight animals were randomly assigned to group 2. Group 1, the control group, was treated with saline while Group 2, the experimental group, was treated with DNA-encoding human HSP90 (FIG. 1).

Figure 1:
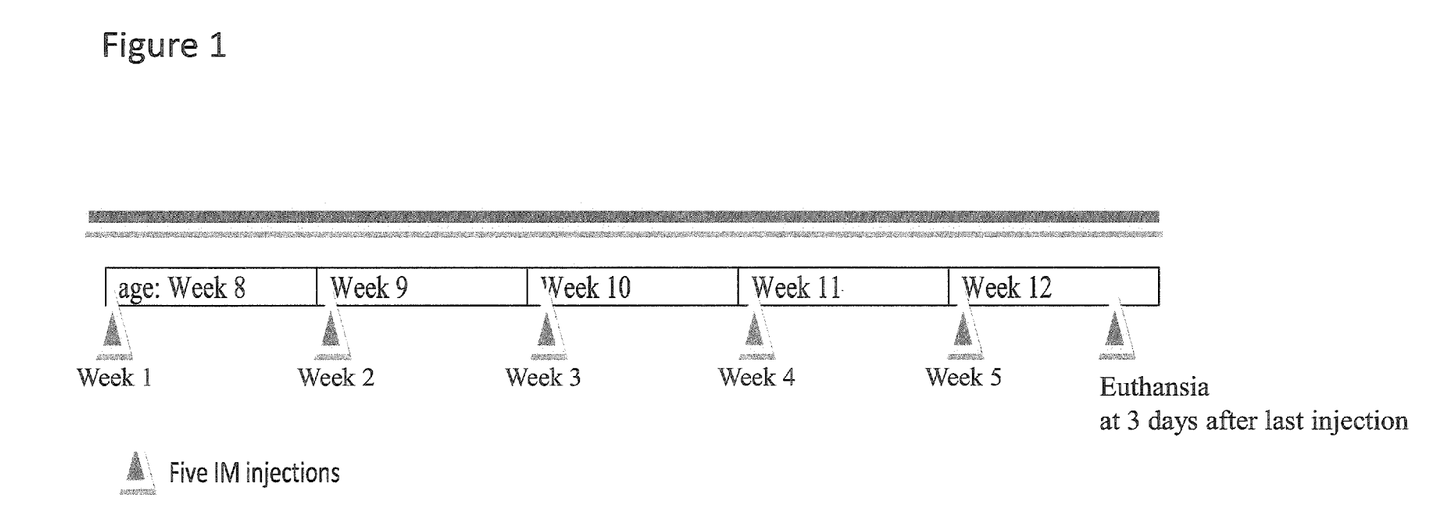
FIG. 1 schematically illustrates the protocol for a five-week treatment of HLA-B27 rats with HSP90. Eight-week old rats received IM injections once a week for five weeks. Animals were euthanized on week 5, three days after receiving their last injection.

Animals were euthanized by cervical dislocation at day 3 following the last injection upon completion of the treatment (FIG. 1).

DNA Plasmids and Buffers, Injection Protocol

DNA-encoding HSP90 was provided as a construct encoding human HSP90 (alpha isoform) in the vector pCDNA3 (obtained from Delphi Genetics SA (batch number DE 160043-160044)) and stored at 4° C. in buffer until ready for use.

Plasmid DNA was prepared by diluting in DNAse/RNAse free PBS buffer pH 7.5 to a concentration of 6 mg/ml and kept at 4° C. during the whole treatment period. Sampling of the solution were made in aseptic conditions using sterile and pyrogen-free material. Briefly, as illustrated in FIG. 1, eight-week old rats were treated weekly over the course of five weeks by intramuscular injection of 200 uL of 0.9% NaCl (Group 1) or 200 uL of 0.25 mg/kg of HSP90 (Group 2). Intramuscular injections were performed on the right and left legs, alternatively following skin preparation with ethyl alcohol swabs to reduce skin bacterial counts.

Clinical Examination

Each animal was checked for clinical signs once a week over the course of the five week treatment period. Each animal's body weight was recorded twice a week starting at the first week of the treatment period until euthanasia.

Example 1: Effect of HSP90-Encoding DNA on Colonic Inflammation

As discussed above, eight-week old rats were treated weekly over the course of five weeks by intramuscular injection of 200 uL of 0.9% NaCl (Group 1, saline control) or 200 uL of 0.25 mg/kg of HSP90 (Group 2). Animals were euthanized at day 3 following the last injection upon completion of the treatment.

To evaluate the effect of HSP90 on colonic inflammation, several parameters were monitored daily during the five-week treatment period. The parameters were assigned scores and the scores were used to calculate a disease activity index (DAI) ranging between 0 and 5. The parameters used included weight loss, stool consistency, and blood occurrence in the animals' stool. No weight loss was assigned a score of 0, less than 10% weight loss was assigned a score of 1 and 10% or more weight loss was assigned a score of 2. A score of 0 was assigned for regular stool consistency, a score of 1 for soft stool consistency and a score of 2 for diarrhea. Blood occurrence observed in the animal's feces was assigned a score of 1 while the absence of blood was assigned a score of 0. DAI was calculated by adding the scores for the parameters for weight loss, stool consistency and blood occurrence. Table 1 provides a summary of the parameters in calculating DAI.

TABLE 1

| Scoring Disease Activity Index | | |
|---|---|---|
| | Parameters | Scores |
| Disease Activity Index (DAI) (0-5) | Weight loss | 0: no; 1: <10%; 2: >10% |
| | Stool consistency | 0: regular; 1: soft; 2: diarrhea |
| | Blood occurrence | 0: absence; 1: presence |

Figure 2:
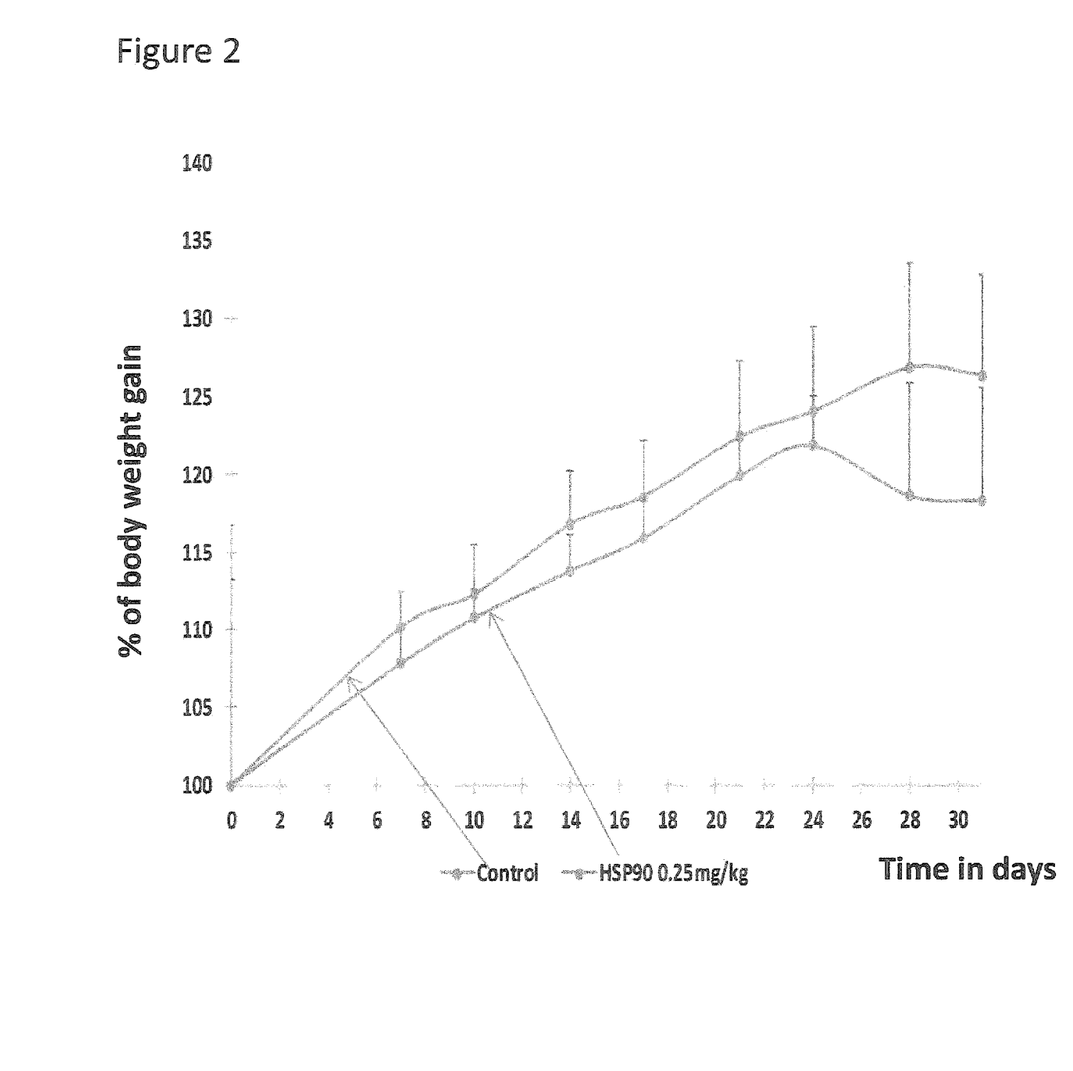
FIG. 2 shows the results of a study to evaluate body weight of HLA-B27 rats treated with 0.25 mg/kg of HSP90-encoding DNA compared to HLA-B27 rats treated with the saline control.

FIG. 2 provides the results of the effect of HSP90-encoding DNA on weight. As shown in FIG. 2, there was no significant difference for the body weight evolution in the group of rats treated with DNA encoding HSP90 as compared to control rats.

Figure 3A:
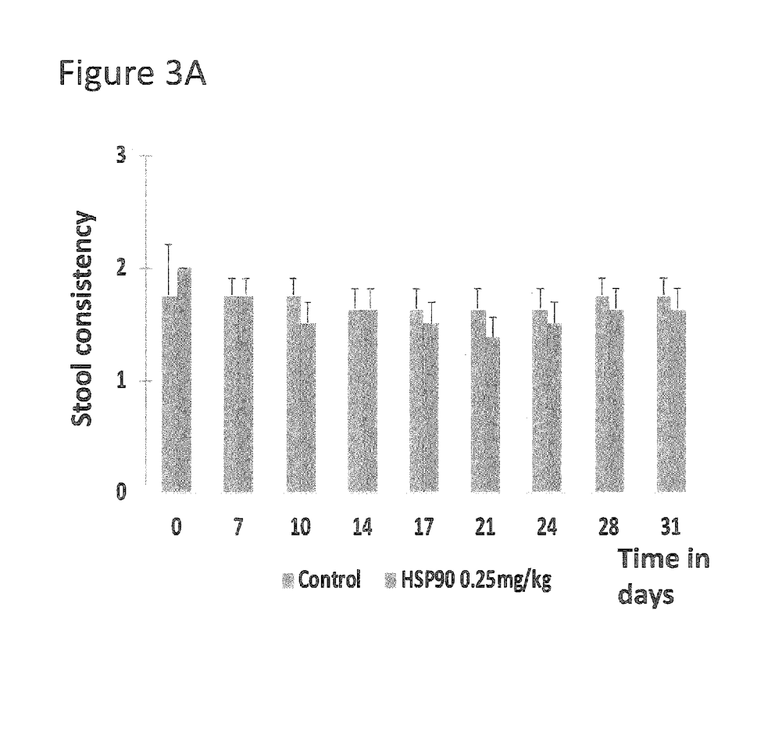
FIGS. 3A-3B shows the results of a study to evaluate the consistency of stool collected from HLA-B27 rats treated with 0.25 mg/kg of HSP-90 as compared to that of HLA-B27 rats treated with saline control. At each time point in FIG. 3A, the control value is shown by the left hand bar and the treatment value (HSP90 0.25 mg/kg) is shown by the right hand bar.
Figure 3B:
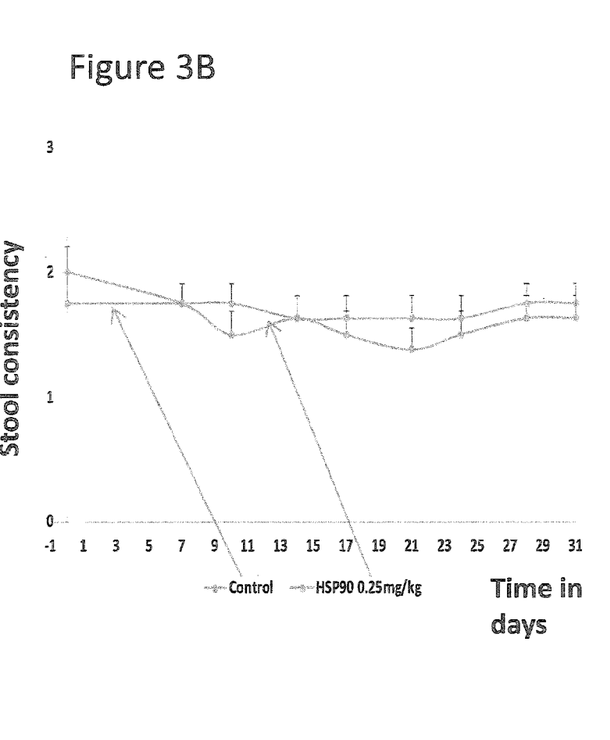

FIGS. 3A and 3B provide the results of analysis of stool consistency. As expected in HLA-B27 rats, a high score for the stool consistency (diarrhea) was observed since the beginning of the study. No significant difference in this parameter was observed in HLA-B27 treated rats compared to control HLA-B27 rats. In HLA-B27 rats treated with HSP-90 at 0.25 mg/kg, no improvement of this parameter was observed even in the end of the study.

Example 2: Evaluation of Effect of HSP90-Encoding DNA on Intensity of Colonic Lesions at the Macroscopic Level To determine the intensity of inflammation in the colon, several parameters were scored after euthanasia of the animals, 3 days after the last week of treatment (week 12+3 days). The parameters were assigned scores and the scores were used to calculate a score ranging between 0 and 11 to represent macroscopic evaluation of the colonic lesions. The parameters included mucosal lesions, colonic hypervascularization, colon wall thickness, and mesentery thickness. Mesentery thickness refers to the region of the mesentery to which the sigmoid colon is attached at the gastrointestinal mesenteric margin. The scoring strategies for the visual assessment of these parameters are summarized in the table below.

TABLE 2

Scoring Macroscopic Evaluation of Colonic Lesions

| | Parameters | Score |
|---|---|---|
| Macroscopic evaluation of the colonic lesions (0-11) | Mucosal lesions | 0: Absence<br>1: Congestive leiong, erythema<br>2: Ulceration <20%, no stenosis<br>3: Ulceration ≥20% no stenosis<br>4: Stenosis |
| | Colonic hypervascularization | 0: Absence<br>1: Moderate<br>2: Diffuse |
| | Colon wall thickness | 0: Normal<br>1: Weak, 1-2 mm<br>2: Moderate, 2-3 mm<br>3: Important, >3 mm |
| | Thickness of the mesocolon and intra-abdominal mesenteric lymph nodes | 0: Absence<br>1: Moderate<br>2: Diffuse |

The results are summarized in the table below.

TABLE 3

Analysis of Parameters for Global Macroscopic Score

| Group | Sex | ID number | Mucosal lesions | hypervascu-larization | colonic wall thickness | mesentery thickness |
|---|---|---|---|---|---|---|
| Control IM PBS | M | 208 | 2 | 1 | 2 | 1 |
| | M | 209 | 0 | 1 | 2 | 2 |
| | M | 211 | 0 | 0 | 0 | 0 |
| | F | 210 | 0 | 0 | 2 | 1 |
| | F | 212 | 0 | 1 | 1 | 1 |
| | F | 213 | 0 | 0 | 1 | 0 |
| | M | 215 | 0 | 1 | 2 | 2 |
| | F | 220 | 0 | 2 | 2 | 1 |
| HSP90 0.25 mg/kg IM 1X/week | M | 198 | 0 | 0 | 0 | 0 |
| | M | 200 | 0 | 0 | 1 | 0 |
| | F | 201 | 0 | 0 | 1 | 1 |
| | F | 204 | 0 | 0 | 1 | 0 |
| | F | 205 | 2 | 0 | 1 | 0 |
| | F | 207 | 0 | 0 | 1 | 0 |
| | M | 218 | 0 | 0 | 1 | 0 |
| | F | 222 | 0 | 0 | 1 | 0 |

Figure 4A:
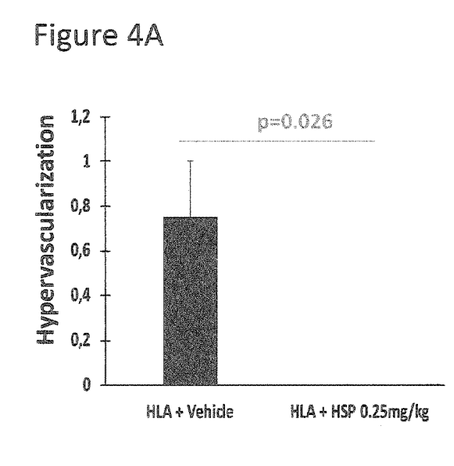
FIGS. 4A-4D depicts scores for the parameters of colonic hypervasculaization (FIG. 4A), thickness of the colonic wall (FIG. 4B), mesentery thickness in colon sample (FIG. 4C), and the global macropscopic score (FIG. 4D) in treated and control animals.
Figure 4B:
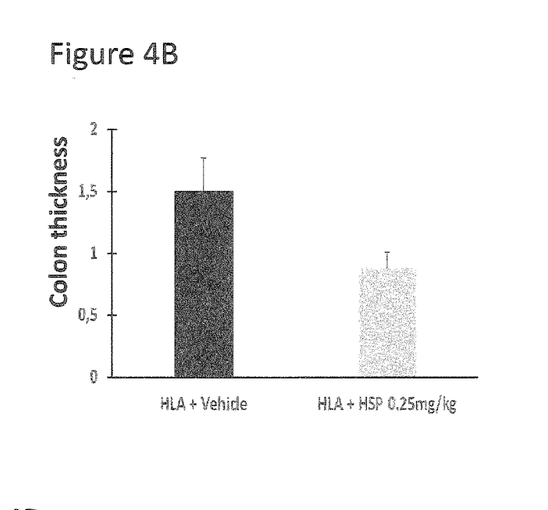
Figure 4C:
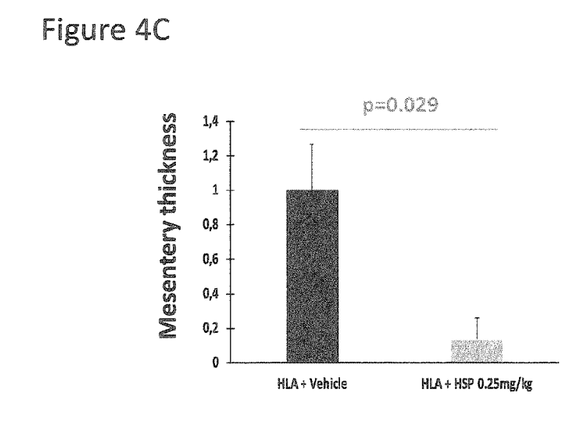
Figure 4D:
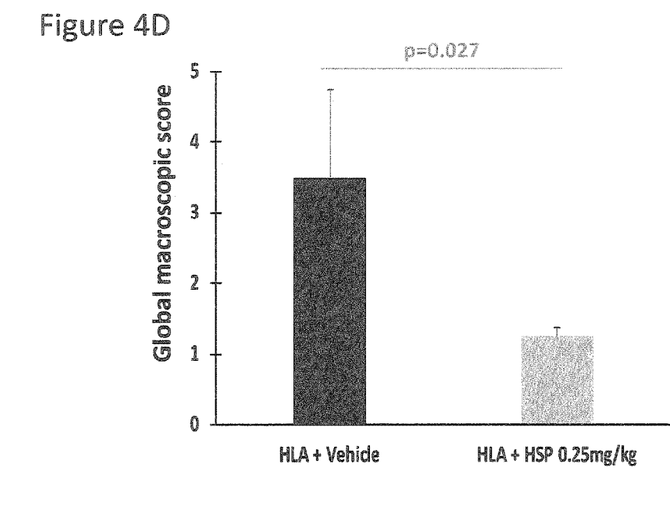

As shown in FIG. 4A, HSP90 treatment significantly decreased the hypervascularization as compared to control. In addition, HSP90 treatment significantly decreased the thickness of mesentery as compared to control (FIG. 4C). In addition, a strong trend to decrease the thickness of the colonic wall was observed in HSP90 treated rats compared to control rats (FIG. 4B). As reflected by the global macroscopic score in shown in FIG. 4D, animal treated with HSP90-encoding DNA exhibited significantly improvement in inflammation as compared to controls.

Example 3: Evaluation of Effect of HSP90-Encoding DNA on Arthritis in the HLA-B27 Transgenic Rats To determine the intensity of arthritis, clinical signs of arthritis in the tarsal joins were monitored daily in all the animals. The clinical signs monitored were swelling and erythema of the hindpaws. Swelling was assessed visually and each animal assigned a score ranging from 0 to 3, a score of 0 was considered normal, a score of 1 was assigned for mild swelling, a score of 2 assigned for moderate swelling, and a score of 3 assigned for severe swelling. The same scoring strategy was followed for erythema of the hindpaws (normal=0, mild=1, moderate=2, severe=3).

Figure 5A:
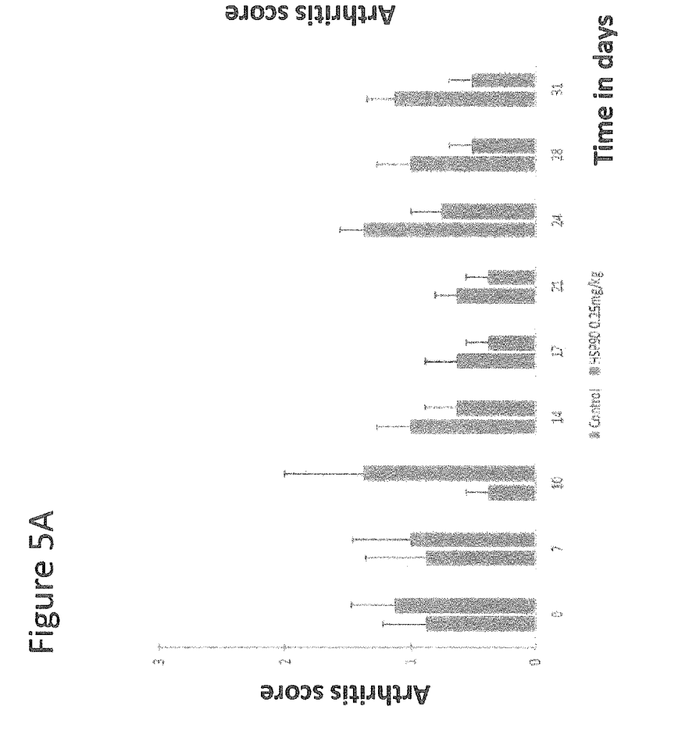
FIGS. 5A-5B depict the results of monitoring the clinical signs of arthritis in the tarsal joints of HLA-B27 rats over the course of the five-week treatment with HSP90 or a control saline solution. At each time point in FIG. 5A, the control value is shown by the left hand bar and the treatment value (HSP90 0.25 mg/kg) is shown by the right hand bar.
Figure 5B:
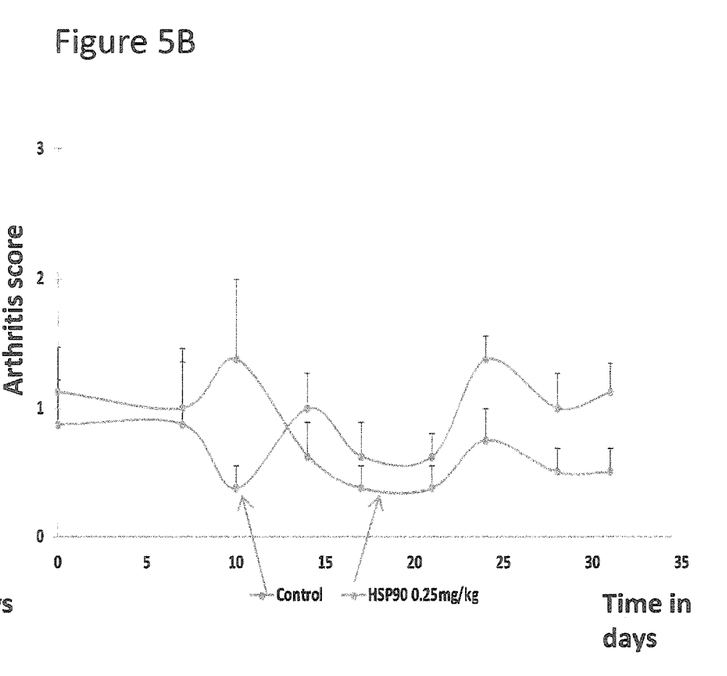

The results of assessment of swelling are shown in FIGS. 5A and 5B. As shown in FIGS. 5A and 8B, a trend toward a decrease in the signs of arthritis was observed in HLA-B27 treated rats as compared to control HLA-B27 rats at day 24 and day 31. In HLA-B27 treated rats an improvement in these signs of arthritis was also observed was observed at day 17 and day 21 of treated animals as compared to the beginning of the study.

Example 4: Evaluation of Effect of HSP90-Encoding DNA on Hematology

For hematology, blood was collected from each animal before the first IM injection (d-1) and at the time of euthanasia (d30) and the following hematology parameters assessed: haematocrit, mean glomerular volume, mean corpuscular hemoglobin content, mean corpuscular hemoglobin concentration, and variability of the size of red cells.

Prior to the first injection, no significant differences regarding the different analyzed parameters between the treatment group of HLA-B27 rats and the control group of HLA-B27 rats were observed, indicating a good homogeneity among the animals in the test and control groups. At day 30, following the 5 injections of HSP90-encoding DNA or saline control, no significant differences were observed, indicating that HSP90 administration did not have a significant effect on the different studied parameters compared to injection of saline control.

In the control HLA-B27 rats, a significant difference was observed for the IDR % at day 30 as compared to prior to injection. In the HLA-B27 rats treated with HSP90-encoding DNA, a significant difference was observed in the number of red corpuscles, the level of hemoglobin, the hematocrit, the CCMH and IDR % at day 30 compared to the levels observed prior to the first injection.

The invention claimed is:

1. A method of treating or preventing a spondyloarthropathy in a subject having, or at risk of developing, the spondyloarthropathy, the method comprising:
provided that the subject is HLA-B27 positive, administering to said subject a composition comprising a nucleic acid molecule encoding a mammalian heat shock protein 90 (HSP90), or an active fragment thereof, wherein the nucleic acid molecule is operatively linked to one or more transcription control sequences.

2. The method of claim 1, comprising:
a) identifying said subject as being HLA-B27 positive, and
b) administering to said HLA-B27 positive subject, the composition comprising the nucleic acid molecule encoding the mammalian HSP90, or active fragment thereof, wherein the nucleic acid molecule is operatively linked to one or more transcription control sequences.

3. The method of claim 2, wherein identifying said subject as being HLA-B27 positive comprises determining the HLA-B27 status of said subject by detection of the HLA-B27 antigen in a sample obtained from said subject.

4. The method of claim 1, wherein said composition is administered to said subject in an amount and for a period of time to provide for improvement in at least one disease symptom of said spondyloarthropathy.

5. The method of claim 1, wherein the spondyloarthropathy is anklyosing spondylitis, reactive arthritis, psoriatic arthritis or enteropathic arthritis.

6. The method of claim 5, wherein said spondyloarthropathy is anklyosing spondylitis.

7. The method of claim 1, wherein said subject is a human.

8. The method of claim 7, wherein said subject is male.

9. The method of claim 7, wherein the mammalian HSP90 is human HSP90.

10. The method of claim 1, wherein said administering is by injection.

11. The method of claim 4, wherein the composition is administered weekly for a period of at least 4 weeks.

12. The method of claim 11, wherein the composition is administered in an amount of from about 0.005 mg/kg to about 1 mg/kg of the nucleic acid molecule encoding the mammalian HSP90, or an active fragment thereof, to the body weight of the subject.

13. The method of claim 12, wherein the composition is administered in an amount of from about 0.01 mg/kg to about 0.5 mg/kg of the nucleic acid molecule encoding the mammalian HSP90, or an active fragment thereof, to the body weight of the subject.

14. The method of claim 12, wherein the composition is administered in an amount of from about 0.10 mg/kg to about 0.30 mg/kg of the nucleic acid molecule encoding the mammalian HSP90, or an active fragment thereof, to the body weight of the subject.

15. The method of claim 1, wherein the nucleic acid molecule is not encapsulated and is not contained in a virus.

16. The method of claim 1, wherein the composition comprises a pharmaceutically acceptable alkali metal salt.

17. The method of claim 16, wherein the pharmaceutically acceptable alkali metal salt is sodium chloride.

18. The method of claim 1, wherein the composition comprises a delivery vehicle selected from the group consisting of a liposome, a micelle, and an emulsion.

19. The method of claim 1, wherein the composition comprises a lipid particle.

20. The method of claim 1, wherein the composition comprises a cationic lipid, polyethylene glycol, polylysine, poloxamer, chitosan, polyL glutamate, or poly(lactide-co-glycolide) (PLG).

* * * * *